(12) United States Patent
Takada et al.

(10) Patent No.: US 8,637,077 B2
(45) Date of Patent: Jan. 28, 2014

(54) SUSTAINED-RELEASE PREPARATION

(75) Inventors: Shigeyuki Takada, Nishinomiya (JP); Masafumi Misaki, Takarazuka (JP); Kenji Nakamura, Itami (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1523 days.

(21) Appl. No.: 10/451,922

(22) PCT Filed: Dec. 26, 2001

(86) PCT No.: PCT/JP01/11420
§ 371 (c)(1), (2), (4) Date: Jun. 27, 2003

(87) PCT Pub. No.: WO02/053136
PCT Pub. Date: Jul. 11, 2002

(65) Prior Publication Data
US 2004/0057996 A1 Mar. 25, 2004

(30) Foreign Application Priority Data

Dec. 28, 2000 (JP) ................................. 2000-402157

(51) Int. Cl.
*A61K 9/22* (2006.01)
*A61K 9/14* (2006.01)

(52) U.S. Cl.
USPC .......................................... 424/468; 424/484

(58) Field of Classification Search
USPC ................................................... 424/468, 484
See application file for complete search history.

(56) References Cited

U.S. PATENT DOCUMENTS

| | | | |
|---|---|---|---|
| 3,832,465 A | | 8/1974 | Ghadimi |
| 5,876,756 A | * | 3/1999 | Takada et al. ............... 424/489 |
| 6,482,864 B1 | * | 11/2002 | Yamagata et al. ......... 514/772.4 |

FOREIGN PATENT DOCUMENTS

| | | |
|---|---|---|
| EP | 82481 | 6/1983 |
| EP | 0 350 246 | 1/1990 |
| EP | 448146 | 9/1991 |
| EP | 0 486 959 A1 | 5/1992 |
| EP | 633020 | 1/1995 |
| EP | 0 709 085 | 5/1996 |
| EP | 905143 | 3/1999 |
| GB | 1 033 378 | 6/1966 |
| WO | 92/11844 | 7/1992 |
| WO | 93/23065 | 11/1993 |
| WO | 93/25221 | 12/1993 |
| WO | 95/29664 | 11/1995 |
| WO | 96/07399 | 3/1996 |
| WO | WO-96/07399 | * 3/1996 |
| WO | WO 96/07399 | * 3/1996 |
| WO | 96/40072 | 12/1996 |
| WO | 96/40074 | 12/1996 |
| WO | 97/01331 | 1/1997 |
| WO | WO 97/01332 | * 1/1997 |
| WO | 97/23217 | 7/1997 |
| WO | 97/23239 | 7/1997 |
| WO | 97/35563 | 10/1997 |
| WO | 98/27980 | 7/1998 |
| WO | 98/43664 | 10/1998 |
| WO | 98/56426 | 12/1998 |
| WO | WO 98/56426 | * 12/1998 |
| WO | 99/33490 | 7/1999 |
| WO | 99/48519 | 9/1999 |
| WO | 00/72830 | 12/2000 |

OTHER PUBLICATIONS

Parkins et al. ("The formulation of biopharmaceutical products" in Pharmaceutical Science & Technology Today, vol. 3, Issue 4, Apr. 1, 2000, pp. 129-137).*
Curatolo et al. (Advanced Drug Delivery Reviews, Vo. 8, Issue 1, Jan.-Feb. 1992, pp. 39-92).*
Supplementary European Search Report, mailed Apr. 10, 2008, in Application No. 01272531.2-1219.
European Office Action issued Sep. 4, 2013 in corresponding European Application No. 01 272 531.3.

* cited by examiner

*Primary Examiner* — Blessing M Fubara
(74) *Attorney, Agent, or Firm* — Wenderoth, Lind & Ponack, L.L.P.

(57) ABSTRACT

Sustained release preparations, which show suppressed initial release of a physiologically active substance and can release a constant amount of the physiologically active substance over a long period of time, and dispersion vehicle thereof can be obtained by adding a cationic substance or polyols to the outside of a matrix or dispersion vehicle thereof. Thus, sustained release preparations, which show suppressed initial release of a physiologically active substance immediately after the administration and can release a constant amount of the physiologically active substance over a long period of time and dispersion vehicle thereof can be provided.

18 Claims, No Drawings

SUSTAINED-RELEASE PREPARATION

TECHNICAL FIELD

The present invention relates to a sustained-release preparation in which the initial release immediately after administration is decreased and a constant amount of bioactive substance is released over a long period of time, and a dispersion vehicle therefor and the like.

BACKGROUND ART

Bioactive peptides are known to exhibit various pharmacological actions in a living body, and are intended to apply for pharmaceuticals. However, these bioactive peptides must be administered frequently since they have generally short half-life in a living body, therefore physical burden of patients due to the frequent injections can be considerable. For example, growth hormone (hereinafter referred to as GH), a representative hormone which is originally produced and secreted in the anterior pituitary gland, is a bioactive peptide having widely diverse physiological activities such as growth stimulation in the body, metabolism of glucose and lipids, anabolism of protein, and cell proliferation and differentiation. The GH has been recently produced on a large scale with *Escherichia coli* using genetic recombination technology, and put to clinical use worldwidely as medicine. However, GH must be frequently administered in order to maintain an effective blood level because of its short biological half-life. Especially, in the case of GH– deficient short stature, practically GH is administered daily by subcutaneous injection to infants or young patients over a long period of time ranging from a few months to 10 years or more.

In order to deal with the problems inherent in bioactive peptide medicine, various drug delivery systems have been studied. For example, a sustained-release agent that provides sustained-release of a bioactive peptide for a long period is exemplified. JP 8-217691 A (WO96/07399) discloses a production method for a sustained-release preparation containing a water-insoluble or poorly water-soluble multivalent metal salt and a biodegradable polymer, wherein the metal salt is formed from a water-soluble peptide bioactive substance and an aqueous solution of zinc chloride and the like. Furthermore, JP 11-322631 A discloses a production method for a sustained-release preparation comprising adding a water-miscible organic solvent and/or a volatile salt to an aqueous solution of a bioactive peptide, followed by lyophilizing to obtain bioactive peptide powder, dispersing the powder in a solution of a biodegradable polymer in an organic solvent, and removing the organic solvent. Moreover, in a production method for a sustained-release microcapsule containing a bioactive substance and a biodegradable polymer, JP 9-132524 A discloses a production method for providing a sustained-release preparation which contains very little residual organic solvent and has very superior clinical characteristics as a medicine, comprising forming microcapsules and heat-drying the microcapsules at the temperature of not less than the glass transition temperature of the biodegradable polymer for about 24 to 120 hr.

OBJECT OF THE INVENTION

A sustained-release preparation is desired to maintain the activities of a bioactive substance while releasing a constant amount of bioactive substance over a long period of time. Therefore, a mean for suppressing the initial release immediately after administration has been required.

SUMMARY OF THE INVENTION

The present inventors have conducted intensive studies to solve the above-mentioned problems, and found that, in the coexistence of a cationic substance or a polyol with a matrix such as microcapsules and the like in a sustained-release preparation containing a micronized bioactive substance obtained by adjusting the concentration of an alkaline metal ion to not more than about 10 μg/mL and a biodegradable polymer, a sustained-release preparation having very superior clinical characteristics as a medicine in which the initial release of the bioactive substance immediately after administration is markedly suppressed and a constant amount of bioactive substance is released over a long period of time, can be produced unexpectedly, which resulted in the completion of the present invention.

Namely, the present invention provides (1) a sustained-release preparation wherein the initial release of the bioactive substance is suppressed, comprising a combination of a matrix containing a bioactive substance and a cationic substance and/or a polyol;

(2) the sustained-release preparation according to the above-mentioned (1), comprising a mixture of a matrix containing a bioactive substance and a cationic substance and/or a polyol;

(3) the sustained-release preparation according to the above-mentioned (1), wherein the cationic substance and/or polyol are retained on the surface of the matrix containing a bioactive substance;

(4) the sustained-release preparation according to the above-mentioned (1), wherein the cationic substance is a basic substance or a water-soluble multivalent metal salt;

(5) the sustained-release preparation according to the above-mentioned (4), wherein the basic substance is a basic amino acid;

(6) the sustained-release preparation according to the above-mentioned (5), wherein the basic amino acid is arginine or lysine;

(7) the sustained-release preparation according to the above-mentioned (4), wherein the basic substance is a basic additive;

(8) the sustained-release preparation according to the above-mentioned (7), wherein the basic additive is benzalkonium chloride or N-methylglucamine;

(9) the sustained-release preparation according to the above-mentioned (4), wherein the basic substance is a basic peptide, a basic polyamine or a basic polysaccharide;

(10) the sustained-release preparation according to the above-mentioned (9), wherein the basic peptide is a protamine or a salt thereof;

(11) the sustained-release preparation according to the above-mentioned (9), wherein the basic polyamine is a spermidine or a spermine;

(12) the sustained-release preparation according to the above-mentioned (9), wherein the basic polysaccharide is a chitosan;

(13) the sustained-release preparation according to the above-mentioned (4), wherein the water-soluble multivalent metal salt is a water-soluble zinc salt;

(14) the sustained-release preparation according to the above-mentioned (13), wherein the water-soluble zinc salt is zinc chloride or zinc acetate;

(15) the sustained-release preparation according to the above-mentioned (1), wherein the polyol is a polyethyleneglycol or propyleneglycol;

(16) the sustained-release preparation according to the above-mentioned (1), wherein the bioactive substance is a bioactive peptide;

(17) the sustained-release preparation according to the above-mentioned (16), wherein the bioactive peptide has a molecular weight of about 200 to about 500,000;

(18) the sustained-release preparation according to the above-mentioned (16), wherein the bioactive peptide has a molecular weight of about 5,000 to about 500,000;

(19) the sustained-release preparation according to the above-mentioned (16), wherein the bioactive peptide is a hormone, a cytokine, a hematopoietic factor, a growth factor or an enzyme;

(20) the sustained-release preparation according to the above-mentioned (16), wherein the bioactive peptide is a human growth hormone;

(21) the sustained-release preparation according to the above-mentioned (1), wherein a base for the matrix is a biodegradable polymer;

(22) the sustained-release preparation according to the above-mentioned (21), wherein the biodegradable polymer is a homopolymer or a copolymer of α-hydroxycarboxylic acids, or a mixture thereof;

(23) the sustained-release preparation according to the above-mentioned (21), wherein the biodegradable polymer is a copolymer having a composition ratio of lactic acid/glycolic acid of about 100/0 to about 40/60 mol %;

(24) the sustained-release preparation according to the above-mentioned (21), wherein the biodegradable polymer is a homopolymer of lactic acid;

(25) the sustained-release preparation according to the above-mentioned (21), wherein the weight-average molecular weight of the biodegradable polymer is about 3,000 to about 50,000;

(26) the sustained-release preparation according to the above-mentioned (1), wherein the matrix is a microcapsule;

(27) the sustained-release preparation according to the above-mentioned (1), which is for injection;

(28) the sustained-release preparation according to the above-mentioned (1), comprising a matrix containing a bioactive substance; a cationic substance and/or a polyol; and a dispersion vehicle;

(29) a dispersion vehicle containing a cationic substance and/or a polyol, which is for the production of the sustained-release preparation according to the above-mentioned (28);

(30) the dispersion vehicle according to the above-mentioned (29), wherein the cationic substance is a basic substance or a water-soluble multivalent metal salt;

(31) the dispersion vehicle according to the above-mentioned (30), wherein the basic substance is a basic amino acid;

(32) the dispersion vehicle according to the above-mentioned (31), wherein the basic amino acid is arginine or lysine;

(33) the dispersion vehicle according to the above-mentioned (30), wherein the basic substance is a basic additive;

(34) the dispersion vehicle according to the above-mentioned (33), wherein the basic additive is benzalkonium chloride or N-methylglucamine;

(35) the dispersion vehicle according to the above-mentioned (30), wherein the basic substance is a basic peptide, a basic polyamine or a basic polysaccharide;

(36) the dispersion vehicle according to the above-mentioned (35), wherein the basic peptide is a protamine or a salt thereof;

(37) the dispersion vehicle according to the above-mentioned (35), wherein the basic polyamine is a spermidine or a spermine;

(38) the dispersion vehicle according to the above-mentioned (35), wherein the basic polysaccharide is a chitosan;

(39) the dispersion vehicle according to the above-mentioned (30), wherein the water-soluble multivalent metal salt is a water-soluble zinc salt;

(40) the dispersion vehicle according to the above-mentioned (39), wherein the water-soluble zinc salt is zinc chloride or zinc acetate;

(41) the dispersion vehicle according to the above-mentioned (29), wherein the polyol is a polyethyleneglycol or propyleneglycol;

(42) the dispersion vehicle according to the above-mentioned (29), which contains an osmoticum;

(43) the dispersion vehicle according to the above-mentioned (42), wherein the osmoticum is a saccharide or a salt;

(44) the dispersion vehicle according to the above-mentioned (29), which contains a thickening agent;

(45) the dispersion vehicle according to the above-mentioned (44), wherein the thickening agent is a water-soluble polysaccharide;

(46) the dispersion vehicle according to the above-mentioned (29), which contains a surfactant;

(47) the dispersion vehicle according to the above-mentioned (46), wherein the surfactant is a nonionic surfactant;

(48) the dispersion vehicle according to the above-mentioned (29), which is for injection;

(49) a method for suppressing the initial release of a bioactive substance, comprising mixing a cationic substance and/or a polyol with a sustained-release preparation containing a matrix containing a bioactive substance;

(50) a microparticle of a bioactive substance, which is obtained by adjusting the concentration of an alkaline metal ion in a solution of a bioactive substance to not more than about 10 µg/mL;

(51) the microparticle according to the above-mentioned (50), wherein the bioactive substance is a bioactive peptide;

(52) the microparticle according to the above-mentioned (51), wherein the bioactive peptide is a hormone, a cytokine, a hematopoietic factor, a growth factor or an enzyme;

(53) the microparticle according to the above-mentioned (51), wherein the bioactive peptide is a human growth hormone;

(54) the microparticle according to the above-mentioned (50), of which weight-average particle diameter is about 0.5 µm to about 2.0 µm;

(55) a process for producing a microparticle of a bioactive substance, which comprises using a solution of a bioactive substance having a concentration of alkaline metal ion in the bioactive substance solution of not more than about 10 µg/mL;

(56) the microparticle according to the above-mentioned (50), wherein the solution further contains ammonium acetate;

(57) a sustained-release preparation, which contains the microparticle according to the above-mentioned (50);

(58) the sustained-release preparation according to the above-mentioned (57), wherein the base of the sustained-release preparation is a biodegradable polymer;

(59) the sustained-release preparation according to the above-mentioned (58), wherein the biodegradable polymer is a homopolymer or a copolymer of α-hydroxycarboxylic acids, or a mixture thereof;

(60) the sustained-release preparation according to the above-mentioned (58), wherein the biodegradable polymer is a copolymer having the composition ratio of lactic acid/glycolic acid of about 100/0 to about 40/60 mol %;

(61) the sustained-release preparation according to the above-mentioned (58), wherein the biodegradable polymer is a homopolymer of lactic acid;

(62) the sustained-release preparation according to the above-mentioned (58), wherein the weight-average molecular weight of the biodegradable polymer is about 3,000 to about 50,000; and

(63) the sustained-release preparation according to the above-mentioned (57), which is a microcapsule.

DETAILED DESCRIPTION OF THE INVENTION

The bioactive substance in the present invention includes, and not specifically limited to, for example peptide compounds having bioactivity (hereinafter referred to 'bioactive peptide'), other antibiotics, antifungal agents, antihyperlipidemic agents, antitumor agents, antipyretic agents, analgesic agents, antiinflammatory agents, antitussive and expectorant agents, sedatives, muscle relaxants, anticonvulsants, antiulcer agents, antidepressants, antiallergic agents, cardiotonics, antiarrhythmic agents, vasodilators, hypotensive diuretics, antidiabetic agents, anticoagulants, hemostatic agents, antiplatelet agents, antituberculous agent, hormones, antinarcotics, bone resorption-suppressing agents, osteogenesis-accelerating agents, neovascularization suppressing agents and the like. Among these, peptide compound is specifically preferred.

The bioactive peptide in the present invention includes various peptides or proteins, which have physical activities useful for mammals and can be used clinically. The "bioactive peptide" having a molecular weight as monomers of, for example, about 200 to 500,000, preferably molecular weight of about 1,000 to 500,000, is generally used. More preferably, a peptide having a molecular weight of 5,000 to about 500,000 is used.

Typical activity of the bioactive peptide includes hormone action. The bioactive peptide may be a natural substance, a synthetic substance or a semi-synthetic substance, or may be a derivative or an analogue thereof. The action mechanism of the bioactive peptide may be either agonistic or antagonistic.

As the bioactive peptide of the present invention, for example peptide hormones, cytokines, peptide neurotransmitters, hematopoietic factors, various growth factors, enzymes, peptide antibiotics, analgetic peptides and the like are used.

As the peptide hormones, for example insulin, somatostatin, somatostatin derivatives (Sandostatin; see U.S. Pat. Nos. 4,087,390, 4,093,574, 4,100,117 and 4,253,998), growth hormones (GH), sodium diuretic peptides, gastrin, prolactin, adrenocorticotropic hormone (ACTH), ACTH derivatives (e.g., ebiratide and the like), melanocyte-stimulating hormone (MSH), thyrotropin-releasing hormone (TRH) and salts and derivatives thereof (see JP 50-121273 A and 52-116465 A), thyroid-stimulating hormone (TSH), luteinizing hormone (LH), follicle-stimulating hormone (FSH), human chorionic gonadotropin (HCG), thymosin, motilin, vasopressin, vasopressin derivatives [desmopressin, see Folia Endocrinologica Japonica, Vol. 54, No. 5, pp. 676-691 (1978)], oxytocin, calcitonin, parathyroid hormone (PTH), glucagon, secretin, pancreozymin, cholecystokinin, angiotensin, human placental lactogen, glucagon-like peptide (GLP-1) and derivatives thereof (see JP 6-80584 A, JP 7-2695 A, EP658568, JP 8-245696 A, JP 8-269097, WO97/15296, WO97/31943, WO98/19698, WO98/43658, JP 10-511365 A, WO99/55310, JP 11-513983 A, CA2270320, WO99/64061, JP 11-514972 A, JP 2000-500505 A, WO2000/66138, WO2000/66142, WO2000/78333, JP 2001-11095 A, Tissue Eng. 7(1)35-44(2001), Diabetologia 43(10)1319-1328 (2000), WO2000/34331, WO2000/34332, U.S. Pat. No. 6,268,343, US 2001011071 A, US 2001006943 A, EP0733644, WO2000/77039, WO99/43707, WO99/43341, WO99/43706, WO99/43708, WO99/43705, WO99/29336, WO2000/37098, EP0969016, U.S. Pat. No. 5,981,488, U.S. Pat. No. 5,958,909, WO93/25579, WO98/43658, EP0869135, U.S. Pat. No. 5,614,492, U.S. Pat. No. 5,545,618, U.S. Pat. No. 5,120,712, U.S. Pat. No. 5,118,666, WO95/05848, WO91/11457, EP0708179, WO96/06628, EP0658568, WO87/06941), Metastin and derivatives thereof (see WO2000/24890) and the like, are used. The peptide hormone preferably includes insulin and growth hormone and the like.

The cytokines include, for example, lymphokines, monokines and the like. The lymphokines include, for example, interferons (alpha, beta, gamma and the like) and interleukins (e.g., IL-2, 3, 4, 5, 6, 7, 8, 9, 10, 11, 12 and the like) and the like. The monokines include, for example, interleukin-1 (IL-1), tumor necrosis factor (TNF) and the like. The cytokine is preferably a lymphokine and the like, more preferably interferon and the like, especially preferably interferon-alpha.

The peptide neurotransmitters include, for example, substance P, serotonin, GABA and the like.

The hematopoietic factors include, for example, erythropoietin (EPO), colony stimulating factors (G-CSF, GM-CSF, M-CSF and the like), thrombopoietin (TPO), platelet-derived growth factor, megakaryocyte potentiator and the like.

The various growth factors include, for example, basic and acidic fibroblast growth factors (FGF) and their families (e.g., EGF, TGF-α, TGF-β, PDGF, acidic FGF, basic FGF, FGF-9 and the like), nerve growth factor (NGF) and its family (e.g., BDNF, NT-3, NT-4, CNTF, GDNF and the like), insulin-like growth factors (e.g. IGF-1, IGF-2 and the like), bone morphogenetic protein (BMP) and its family and the like.

The enzymes include, for example, superoxide dismutase (SOD), urokinase, tissue plasminogen activator (TPA), asparaginase, kallikrein and the like.

The peptide antibiotics include, for example, polymixin B, colistin, gramicidin, bacitracin and the like.

The analgesic peptides include, for example, enkephalin, enkephalin derivatives (see U.S. Pat. No. 4,277,394 and EP 31567 A), endorphin, kyotorphin and the like.

Further, the bioactive peptides include thymopoietin, dynorphin, bombesin, caerulein, thymostimulin, thymic humoral factor (THF), blood thymic factor (FTS) and derivatives thereof (see U.S. Pat. No. 4,229,438), other thymic factors [Igaku no Ayumi, Vol. 125, No. 10, pp. 835-843 (1983)], neurotensin, bradykinin, and endothelin-antagonistic peptides (see EP 436189 A, 457195 A and 496452 A, and JP 3-94692 A and 3-130299 A) and the like.

The bioactive peptides specifically preferably used for the present invention include luteinizing hormone releasing hormone (LH-RH) and a derivative having the similar action thereto, or LH-RH antagonistic substance, growth hormone, insulin and the like. Among these, growth hormone, especially human growth hormone, is preferred.

In the present invention, when the bioactive peptide contains a metal, the metal contained in the bioactive peptide may be removed previously, if desired. As the method for removing metal, known methods can be used. For example, an insulin in the form of amorphous and containing least amount of metal can be obtained by dialyzing a hydrochloric acidic aqueous solution of insulin to water or a solution of ammonium acetate and lyophilizing the dialysate.

Growth hormone originating from any species can be used, and is preferably human growth hormone. Further, although natural growth hormone extracted from the pituitary gland and the like can be used for the present invention, genetic recombinant GH (see JP 6-12996 B and 6-48987 B) is preferred. The recombinant hGH having the same structure as that of a natural type without methionine at the N-terminal is more preferred. Such GH may be in the form of a metal salt, and the one containing substantially no metal is also used. The hGH having molecular weight of about 20K dalton as well as about 22K dalton (see JP 7-101877 A and 7-265404 A) can be used. Furthermore, the derivatives of hGH or related protein thereof (see WO99/03887) can be used.

While the amount of the bioactive substance in the sustained-release preparation of the present invention varies depending on the kind of the bioactive substance and the like, it is, for example, generally about 0.1 to 50% (W/W), preferably about 0.2 to 30% (W/W), and more preferably about 0.5 to 20% (W/W) in the case of a bioactive peptide.

The matrix in the present invention is a solid containing a bioactive substance in the base (e.g., a biodegradable polymer), which optionally contains an additive, and is a unit that substantially controls sustained-release. Examples thereof include for example a microcapsule, a rod for implantation and the like.

The biodegradable polymer used for the present invention includes polymers synthesized by catalyst-free dehydration polycondensation from one or more of α-hydroxycarboxylic acids (e.g., glycolic acid, lactic acid and the like), hydroxydicarboxylic acids (e.g., malic acid and the like), hydroxytricarboxylic acids (e.g., citric acid and the like) and the like, and having a free carboxyl group or mixtures thereof, poly-α-cyanoacrylic esters, polyamino acids (e.g., poly-γ-benzyl-L-glutamic acid and the like) and maleic anhydride polymers (e.g., a styrene-maleic acid copolymer and the like). These polymers may be a homopolymer or a copolymer. Polymerization type may be of the random, block or graft. When the above-mentioned α-hydroxycarboxylic acids, hydroxydicarboxylic acids and hydroxytricarboxylic acids have an optically active center in their molecules, they may be of the D-, L- or DL-configuration.

Among these polymers, a biodegradable polymer having a free terminal carboxyl group such as polymers synthesized from α-hydroxycarboxylic acids (e.g., glycolic acid, lactic acid and the like) (e.g., polylactic acid, lactic acid-glycolic acid copolymer and the like) and poly-α-cyanoacrylic acid esters are preferred.

The biodegradable polymer is more preferably a polymer synthesized from α-hydroxycarboxylic acids and the like, especially preferably lactic acid-glycolic acid copolymer and the like.

In the present specification, lactic acid-glycolic acid copolymer as well as homopolymers such as polylactic acid and polyglycolic acid are sometimes simply referred to as lactic acid-glycolic acid polymer.

When the biodegradable polymer used is a lactic acid-glycolic acid polymer (a lactic acid-glycolic acid copolymer or homopolymer), its composition ratio (mol %, lactic acid/glycolic acid) is preferably about 100/0 to about 40/60, more preferably about 85/15 to about 50/50.

The weight-average molecular weight of the lactic acid-glycolic acid polymer is preferably about 3,000 to about 50,000, more preferably about 3,000 to about 25,000, further more preferably about 5,000 to about 20,000.

The degree of dispersion (weight-average molecular weight/number-average molecular weight) of the lactic acid-glycolic acid polymer is preferably about 1.2 to about 4.0, more preferably about 1.5 to about 3.5.

Regarding weight-average molecular weight and degree of dispersion in the present specification, the former is the polystyrene reduced value determined by gel permeation chromatography (GPC) using 9 polystyrenes as reference substances with weight-average molecular weights of 120,000, 52,000, 22,000, 9,200, 5,050, 2,950, 1,050, 580 and 162, respectively, and the latter is the calculated value therefrom. The above determination is carried out using a GPC column KF804L×2 (manufactured by Showa Denko K.K.) and an RI monitor L-3300 (manufactured by Hitachi Ltd.) with chloroform as a mobile phase.

A biodegradable polymer having a free terminal carboxyl group is a polymer in which the number-average molecular weight based on terminal group determination and the number-average molecular weight based on GPC measurement above almost correspond with each other. The number-average molecular weight based on terminal group determination is calculated as follows:

About 1 to 3 g of the biodegradable polymer is dissolved in a mixed solvent of acetone (25 ml) and methanol (5 ml), and the solution is quickly titrated with a 0.05 N alcoholic solution of potassium hydroxide under stirring at room temperature (20° C.) with phenolphthalein as an indicator to determine the carboxyl group in the solution; the number-average molecular weight based on terminal group determination is calculated from the following equation:

$$\text{Number-average molecular weight based on terminal group determination} = 20000 \times A/B$$

A: Weight mass (g) of biodegradable polymer
B: Amount (ml) of the 0.05 N alcoholic solution of potassium hydroxide added until titration end point is reached While the number-average molecular weight based on terminal group determination is an absolute value, the number-average molecular weight based on GPC measurement is a relative value that varies depending on various analytical conditions (e.g., kind of mobile phase, kind of column, reference substance, slice width chosen, baseline chosen etc.); it is therefore difficult to have an unique numerical representation. However, that both number-average molecular weights determined by GPC measurement and terminal group determination almost correspond with each other means, for example, that the number-average molecular weight based on terminal group determination falls within the range from about 0.5 to about 2 times, preferably from about 0.7 to about 1.5 times, of the number-average molecular weight based on GPC measurement in a polymer which is synthesized from α-hydroxycarboxylic acids.

For example, in the case of a polymer having a free terminal carboxyl group which is synthesized from one or more α-hydroxycarboxylic acids by catalyst-free dehydration polycondensation, the number-average molecular weight based on GPC measurement and the number-average molecular weight based on terminal group determination almost correspond with each other. On the other hand, in the case of a polymer having substantially no free terminal carboxyl group which is synthesized from a cyclic dimer by ring-opening polymerization using a catalyst, the number-average molecular weight based on terminal group determination is significantly (about 2 times or more) higher than that based on GPC measurement. This difference makes it possible to clearly differentiate a polymer having a free terminal carboxyl group from a polymer having no free terminal carboxyl group.

A lactic acid-glycolic acid polymer having a free terminal carboxyl group can be produced by a per se known process such as that described in JP 61-28521 A (e.g., process by catalyst-free dehydration polycondensation reaction or dehydration polycondensation reaction in the presence of an inorganic solid acid catalyst).

The decomposition/disappearance rate of a lactic acid-glycolic acid polymer varies widely depending on composition ratio or weight-average molecular weight. A release duration of bioactive substance can be extended (e.g., to about 6 months) by lowering the glycolic acid ratio or increasing the molecular weight, since decomposition/disappearance rate is usually delayed as the glycolic acid ratio decreases. Conversely, the release duration can be shortened (e.g., to about one week) by increasing the glycolic acid ratio or decreasing the molecular weight. To obtain a one week to two months type sustained-release preparation, it is preferable to use a lactic acid-glycolic acid polymer whose composition ratio and weight-average molecular weight are within the above-described ranges.

Therefore the composition of a biodegradable polymer used in the present invention is preferably selected according to the targeted kind of a bioactive peptide, the desired sustained-release duration and the like. In a specific example, for example, when GH is used as a bioactive peptide, a lactic acid-glycolic acid polymer is preferably used. The lactic acid-glycolic acid polymer is preferably a lactic acid-glycolic acid-copolymer having a lactic acid/glycolic acid composition ratio (mol %) of about 85/15 to about 50/50, more preferably about 75/25 to about 50/50. The weight-average molecular weight of the lactic acid-glycolic acid copolymer is preferably about 8,000 to about 20,000, more preferably about 10,000 to about 20,000. Further, the degree of dispersion (weight-average molecular weight/number-average molecular weight) of the lactic acid-glycolic acid polymer is about 1.2 to about 4.0, more preferably about 1.5 to about 3.5.

The lactic acid-glycolic acid polymer used can be produced by the known methods such as those described in the above publication and the like. The polymer is preferably the one that is produced by catalyst-free dehydration polycondensation. It is preferable that the lactic acid-glycolic acid polymer (PLGA) wherein the number-average molecular weight based on terminal group determination and the number-average molecular weight based on GPC measurement almost correspond with each other is used.

Further, two kinds of lactic acid-glycolic acid polymers differing in composition ratio and/or weight-average molecular weight may be used in an admixture of given ratio. The example is a mixture of lactic acid-glycolic acid copolymer wherein the composition ratio of lactic acid/glycolic acid (mol %) is about 75/25 and the weight-average molecular weight is about 10,000 and lactic acid-glycolic acid copolymer wherein the composition ratio of lactic acid/glycolic acid (mol %) is about 50/50 and the weight-average molecular weight is about 12,000. The preferred weight ratio of these copolymers in the mixture is about 25/75 to about 75/25, respectively.

The biodegradable polymer used in the present invention can be metal salts of the above mentioned biodegradable polymer. For example, various polyvalent metal salts of the biodegradable polymer and the like described in WO97/01331 can be used. Preferably, polyvalent metal salt of the lactic acid-glycolic acid polymer and the like (more preferably, zinc salt, calcium salt, magnesium salt and the like, further more preferably zinc salt and the like) can be used. The metal of the polyvalent metal salt is not particularly limited as long as it does not cause any adverse effect to a living body, and is exemplified by polyvalent metals such as bivalent metals (e.g., iron, zinc, copper, calcium, magnesium, aluminum, tin, manganese and the like), trivalent metals (e.g., iron, aluminum, manganese and the like), tetravalent metals (e.g., tin and the like) and the like.

In the present specification, not only the biodegradable polymer but also metal salt thereof is sometimes referred to as the biodegradable polymer. For example, a polyvalent metal salt of lactic acid-glycolic acid polymer is also sometimes referred to as lactic acid-glycolic acid polymer.

These polyvalent metal salts of the biodegradable polymer can be produced by the method described in WO97/01331 or similar methods thereto.

In case that polyvalent metal salt of the biodegradable polymer is a zinc salt, it can be produced by reaction of the biodegradable polymer and zinc oxide in an organic solvent.

Concerning the order of addition of biodegradable polymer and zinc oxide into organic solvent, zinc oxide in powder or suspension in organic solvent can be added into the solution of biodegradable polymer in organic solvent, or on the contrary, the solution of the biodegradable polymer in organic solvent can be added into the suspension of zinc oxide in organic solvent. Furthermore, after mixing both of the biodegradable polymer and zinc oxide in powder form, organic solvent can be added thereto.

The content of the biodegradable polymer contained in the sustained-release preparation of the present invention is generally about 30 to 99.9% (W/W), preferably about 60 to 97% (W/W), and more preferably about 70 to 90% (W/W).

In the production of the sustained-release preparation of the present invention, the organic solvent used to dissolve the biodegradable polymer preferably has a boiling point of not more than 120° C. The organic solvent includes, for example, halogenated hydrocarbons (e.g., dichloromethane, chloroform and the like), alcohols (e.g., ethanol, methanol and the like), ethyl acetate, acetonitrile and the like. These solvents may be used in a mixture of a suitable ratio. When one of the organic solvents is used solely, such as dichloromethane, ethyl acetate, acetonitrile and the like are preferred. When the organic solvents are used as a mixed solvent, such as a combination of halogenated hydrocarbons (e.g., dichloromethane, chloroform and the like) and alcohols (e.g., ethanol, methanol and the like) or acetonitrile is preferred. The mixing ratio (volume ratio) of the halogenated hydrocarbons and alcohols or acetonitrile is about 100:1 to about 1:1, and it is desirable to use a mixed solvent having a mixing ratio of preferably about 30:1 to about 2:1. Furthermore, while the concentration of the biodegradable polymer in a solution varies depending on the molecular weight, the kind of organic solvent and the like, it is, for example, about 0.01 to about 80% (W/W), preferably about 0.1 to about 70% (W/W), and more preferably about 1 to about 60% (W/W).

The cationic substance in the present invention is a basic substance or a water-soluble multivalent metal salt.

The basic substance includes basic amino acids (e.g., arginine, lysine and the like), basic peptides (e.g., protamine such as protamine, protamine sulfate, protamine hydrochloride, protamine phosphate and the like, or a salt thereof), basic polyamines (e.g., spermidine, spermine and the like), basic polysaccharides (e.g., chitosan and the like), basic additives (e.g., benzalkonium chloride, N-methylglucamine (Meglumine) and the like) and the like. The water-soluble multivalent metal salt includes water-soluble zinc salts (e.g., zinc chloride, zinc acetate), water-soluble calcium salts, water-soluble magnesium salts and the like.

The polyol in the present invention includes polyethyleneglycol, propyleneglycol and the like.

While the dose (the amount to be added) of the cationic substance and/or polyol in the present invention varies depending on the kinds of the cationic substance and polyol, target animal, administration site and the like, preferably it may be suitably selected from the range of about 0.0001 to about 100 mg/kg body weight per an infant or an adult. The dose (amount to be added) for the cationic substance and polyol is preferably the amount in the range of actual use of the cationic substance and polyol. For example, when the cationic substance is protamine sulfate, the dose of subcutaneous administration for an infant or an adult is preferably the amount of actual use of not more than 3.5 mg. When the cationic substance is arginine, the dose for an infant or an adult is preferably the amount of actual use of not more than 40 mg in the case of subcutaneous administration, or not more than 1620 mg in the case of intramuscular administration.

The content of the cationic substance and/or polyol contained in the sustained-release preparation of the present invention is about 0.0001 to 80% (W/W), preferably about 0.001 to 40% (W/W) and more preferably about 0.01 to 20% (W/W) relative to the whole preparation.

The sustained-release preparation in the present invention is a preparation obtained by forming a matrix and optionally adding an excipient (e.g., mannitol) thereto and treating (e.g., lyophilizing) it.

The initial release rate of the bioactive substance in the present invention is the ratio of the amount of the bioactive substance that has been released within one day after administration of the sustained-release preparation to an animal (rat) relative to the dose.

In the sustained-release preparation of the present invention, the matrix containing a bioactive substance may co-exist with the cationic substance and/or polyol, and therefore the both ingredients may be mixed, or may be contained in separate containers and prepared (suspended) just before use. Alternatively, for example, the three ingredients of the matrix, cationic substance and/or polyol and dispersion vehicle may exist independently in one container (e.g., a dual-chamber prefilled cylinge and the like) without contacting each other and may be mixed immediately before administration.

The cationic substance and/or polyol in the sustained-release preparation of the present invention may not exist in the matrix, and may be retained (attachment) on the surface (outer portion) of the matrix or contained in the dispersion vehicle.

The dispersion vehicle in the present invention is a liquid media used for injecting the sustained-release preparation as a suspension, and is preferably a water-soluble medium. The dispersion vehicle generally contains osmoticums (isotonic agents), viscosity agents (suspending agents), surfactants, preservatives (stabilizers), soothing agents, local anesthetics and the like. As the osmoticums (isotonic agents), for example, sodium chloride, mannitol, sorbitol, glucose and the like are used. As the viscosity agents (suspending agents), for example, carboxymethylcellulose sodium, sodium alginate, hyaluronic acid, polysaccharides such as dextran and the like are used. As the surfactants, for example, Polysolvate 80 (Tween 80), HCO-60 and the like are used. As the preservatives (stabilizers), for example, methylparaben, propylparaben and the like are used. As the soothing agents, for example, benzylalcohol and the like are used. As the local anesthetics, for example, xylocaine hydrochloride, chlorobutanol and the like are used. Furthermore, the dispersion vehicle optionally contains pH adjusting agents (e.g., hydrochloric acid, acetic acid, sodium hydroxide, or various buffers). Not only the above-mentioned aqueous dispersion vehicles but also oily dispersion vehicles are used. Vegetable oils such as sesame oil, corn oil and the like or a mixture thereof with phospholipids such as lecithin and the like or middle chain fatty acid triglycerides (e.g., Miglyol 812) and the like can be used as an oily dispersion vehicle.

The matrix containing a bioactive substance of the present invention is produced by removing the organic solvent from the S/O dispersion liquid in which the powder (S phase) obtained by lyophilizing a solution of bioactive substance has been dispersed in the solution of the biodegradable polymer in the organic solvent (O phase), or removing the solvent from the W/O emulsion in which the aqueous phase (W phase) dissolving the bioactive substance in water has been dispersed in the solution of biodegradable polymer in organic solvent (O phase), or removing the solvent from the solution in which a bioactive substance and a biodegradable polymer have been dissolved in an organic solvent (O phase). The production method includes, for example, (a) in-water drying method (S/O/W method and W/O/W method or O/W method), (b) phase separation method (coacervation method) and (c) spray-drying method, or similar methods thereto and the like. Hereinafter, as a matrix containing a bioactive substance, a production method of, for example, microcapsules is explained.

(a-1) In-Water Drying Method (S/O/W Method)

According to this method, at first a water-miscible organic solvent and/or a volatile salt is added to the aqueous solution of the bioactive substance, and then, the bioactive substance powder (S phase) is produced by lyophilization. On this occasion, in order to obtain fine powder, the salt concentration in the solution of bioactive substance, for example, the ion concentration of an alkali metal (sodium, potassium, calcium and the like) is preferred to be low. For example, when the alkali metal is sodium, its ion concentration is preferably not more than about 10 μg/mL. The biodegradable polymer is then dissolved in the organic solvent, and the above bioactive substance powder is added and dispersed into the resulting organic solvent solution. The ratio (ratio by weight) of the bioactive substance powder and the biodegradable polymer is, for example, about 1:1000 to about 1:1, preferably about 1:200 to about 1:5, more preferably about 1:100 to about 1:5. Preferably, an external physical energy is applied to disperse the bioactive substance powder uniformly into the organic solvent solution. As the method, for example, irradiation of ultrasonic wave, a turbine stirrer, a homogenizer and the like are used. The weight-average particle size of the bioactive substance powder in the organic solvent solution is preferably not more than about 10 μm, more preferably about 0.1 to about 5 μm, further more preferably about 0.5 to about 2 μm, and this is easily achieved by using the bioactive substance powder obtained in the present invention. The weight-average particle size of the bioactive substance powder in the present invention means the value obtained by a laser diffraction particle size analyzer (SALD2000A: Shimadzu Corporation) using the dispersion liquid of the bioactive substance powder in organic solvent such as dichloromethane prepared with a homogenizer. In this process, the bioactive substance powder is added into an organic solvent such as dichloromethane at the concentration of about 20 to 100 mg/mL, and then stirred and dispersed using a homogenizer (e.g., Polytron (manufactured by Kinematica)) at about 20,000 rpm for about 30 sec to 1 min. The resulting dispersion liquid is diluted adequately with the organic solvent into the measurable concentration range of the above laser diffraction particle size analyzer.

Further, the organic solvent dispersion liquid (S/O dispersion liquid) prepared as above mentioned is added into an aqueous solvent (W phase), and then the same external physical energy as above mentioned, for example, irradiation of ultrasonic wave, a turbine stirrer, a homogenizer and the like is applied to form the S/O/W emulsion. Then, the solvent of the oil phase is evaporated to produce the microcapsules. The volume of the water phase is selected from the volume of generally about 1 times to about 10,000 times, preferably about 2 times to about 5,000 times, more preferably about 5 times to about 2,000 times based on the volume of the oil phase.

An emulsifier can be added into the above external water phase. As the emulsifier, can be used any one which is capable of forming the generally stable S/O/W emulsion. The emulsifier includes, for example, anionic surfactants, nonionic surfactants, castor oil polyoxyethylene derivatives, polyvinylpyrrolidones, polyvinyl alcohols, carboxymethyl celluloses, lecithin, gelatin, hyaluronic acids and the like. These emulsifiers can be used in admixture thereof if desired. The concentration of the emulsifer in the external water phase is, preferably about 0.001% to 20% (w/w), more preferably about 0.01% to 10% (w/w), particularly preferably about 0.05% to 5% (w/w).

The thus obtained microcapsules are collected by centrifugation or filtration, washed with distilled water to remove the emulsifier and the like adhering to the surface of microcapsules, re-dispersed in distilled water, and lyophilized.

In the present invention, the water-miscible organic solvent which can be added into the aqueous solution of the bioactive substance, includes, for example, alcohols (e.g. methanol, ethanol, isopropanol and the like, preferably methanol, ethanol and the like), acetone and the like. These organic solvents can be used in admixture thereof in a suitable mixing ratio, but alcohol, especially ethanol is preferably used alone. The amount of addition (concentration) of the water-miscible organic solvent to the aqueous solution of the bioactive substance is about 0.03 to 0.5% (V/V), preferably about 0.06 to 0.25% (V/V), more preferably about 0.1 to 0.15% (V/V), by volume-ratio. By lyophilizing the aqueous solution of bioactive substance obtained by adding the water-miscible organic solvent, the bioactive substance powder can be prepared, which is easy to handle (superior in handling) and is very fine (has a small particle size).

The volatile salt to be added into the aqueous solution of the bioactive substance in this method includes, for example, ammonium salt (e.g., ammonium acetate, ammonium bicarbonate, ammonium carbonate, ammonium chloride and the like, preferably ammonium acetate and the like). These salts can be used in admixture thereof in an appropriate ratio. The amount of addition of the volatile salt to the aqueous solution of the bioactive substance is about 10 times to about 80 times mole, preferably about 10 times to about 70 times mole, more preferably about 15 times to about 70 times mole, further more preferably about 20 times to about 70 times mole, and the most preferably about 20 times to about 50 times mole by mole ratio. Similar to the case that the water-miscible organic solvent is added, by lyophilizing the aqueous solution of the bioactive substance obtained by adding the volatile salt, the bioactive substance powder can be prepared, which is easy to handle (superior handling) and is very fine (has a small particle size).

In the present method, the water-miscible organic solvent and/or volatile salt added to the aqueous solution of the bioactive substance can be used solely or in admixture thereof. When the water-miscible organic solvent and the volatile salt are used in combination, they can be added into the aqueous solution of the bioactive substance in accordance with the above amount of addition respectively.

(a-2) In-Water Drying Method (W/O/W Method)

According to this method, water or suitable buffer is added to a bioactive substance to give a solution of bioactive substance (W phase). A biodegradable polymer is then dissolved in an organic solvent, and to this organic solvent solution is added the above-mentioned solution of bioactive substance and is dispersed. The thus-obtained W/o emulsion is added to an aqueous solvent (W phase). As with the above-mentioned S/O/W method, microcapsules are obtained from W/O/W emulsion.

(a-3) In-Water Drying Method (O/W Method)

According to this method, a biodegradable polymer and a bioactive substance are dissolved in an organic solvent. The organic solvent solution (O phase) is then added to an aqueous solvent (W phase), and as with the above-mentioned S/O/W method, microcapsules are obtained from O/W emulsion.

(b) Phase Separation Method (Coacervation Method)

In this method, a coacervating agent is gradually added to the S/O dispersion liquid of (a-1) or the W/O emulsion of (a-2) or oil phase solution of (a-3) described above under stirring to precipitate and solidify microcapsules. The amount of the coacervating agent to be added is about 0.01 to about 1,000 times by volume, preferably about 0.05 to about 500 times by volume, especially preferably about 0.1 to about 200 times by volume. Any coacervating agent can be used, as long as it is a polymeric, mineral oil or vegetable oil compound miscible with the organic solvent for dissolution of a biodegradable polymer and does not dissolve the biodegradable polymer used. Specifically, examples of such coacervating agents include silicone oil, sesame oil, soybean oil, corn oil, cottonseed oil, coconut oil, linseed oil, mineral oil, n-hexane, n-heptane and the like. Two or more of these can be used in combination. The thus obtained microcapsules are collected by filtration, washed repeatedly with heptane and the like to remove the coacervating agent. Further, washing is conducted in the same manner as in the above (a), followed by lyophilization.

In the production of microcapsules by the drying-in-water method or coacervation method, an antiaggregation agent can be added for preventing aggregation of particles. As examples of the antiaggregation agent, for example, water-soluble polysaccharides such as mannitol, lactose, glucose, starches (e.g., corn starch and the like), hyaluronic acid and its alkali metal salt; proteins such as glycine, fibrin and collagen; and inorganic salts such as sodium chloride, sodium hydrogen phosphate and the like can be used.

(c) Spray-Drying Method

In the present method, the S/O dispersion liquid of (a-1), the W/O emulsion of (a-2) or the oil phase solution of (a-3), described above, is sprayed via a nozzle into the drying chamber of a spray drier to volatilize the organic solvent in the fine droplets in a very short time to produce microcapsules. Such nozzles include, for example, a two-fluid nozzle, a pressure nozzle, a rotary disc and the like. It is also advantageous, if necessary, to spray an aqueous solution of the above-described antiaggregation agent via another nozzle simultaneously with spraying the above dispersion liquid in order to prevent aggregation of each microcapsule particles. The thus-obtained microcapsules are further washed as with the above-mentioned (a), and optionally heated (under reduced pressure, if desired) to remove water and organic solvents further.

As a method for preparation of the rod for implantation as the matrix containing a bioactive substance in the present invention, a method comprising heating the mixture of the bioactive substance and the base to the temperature not less than the glass transition temperature of the base and then molding in a mold or forming by extrusion and the like is exemplified. The shape thereof may be selected from any shapes in addition to rod type. Alternatively, the rod-shaped preparation for implantation can be prepared by pulverizing or microcapsulating the mixture of the bioactive substance and the base by a certain method in advance, filling the mixture in a stainless tube or a Teflon tube and compressing to mold the mixture. On this occasion, if necessary, the mixture may be heated to the temperature not less than the glass transition temperature of the base. For example, a rod-shaped preparation having an outer diameter of 2.0 mm can be obtained by filling the microcapsules obtained by the drying-in-water method in a Teflon tube having an inner diameter of 2.0 mm, heating at 60° C. for 15 min, compressing the microcapsules with a rod having a diameter of 2.0 mm, cooling and forming the compressed microcapsules.

The sustained-release preparation of the present invention is preferably in the form of microparticles. This is because the sustained-release preparation does not provide undue pain to a patient when it is administered to said patient using an injection needle generally used for subcutaneous or intramuscular injection. The particle size of the sustained-release preparation is, for example, about 0.1 to 300 μm, preferably about 1 to 150 μm, specifically preferably about 2 to 100 μm as the mean particle diameter. Although varying depending on the kind of the bioactive substance and the like, the content of the bioactive substance in the sustained-release preparation of the present invention is, for example, in the case of bioactive peptide, generally about 0.1 to 50% (W/W), preferably about 0.2 to 30% (W/W), and more preferably about 0.5 to 20% (W/W). The content of the biodegradable polymer contained in the sustained-release preparation of the present invention is generally about 30 to 99.9% (W/W), preferably about 60 to 97% (W/W), and more preferably about 70 to 90% (W/W).

The initial release percentage of the bioactive substance in the sustained-release preparation of the present invention [the release percentage up to one day (24 hr) after administration] is preferably not more than about 50%, more preferably about 1% to about 30%, more preferably about 2% to about 20%, and the most preferably about 2% to about 15% of the dose administered. The initial release percentage is obtained by obtaining the amount of initial release by applying the AUC (Area Under the ConcentrationTime Curve) of the blood concentration of the sustained-release preparation of the present invention up to 24 hrs after subcutaneous administration to the dose-AUC straight line that has been obtained from the AUC up to 24 hr after subcutaneous administration of the bioactive substance solution, and then calculating the initial release percentage.

The sustained-release preparation of the present invention can be administered, for example, as a microcapsule or, by preparing various dosage forms using the microcapsule as a raw material, as parenteral preparations (e.g., injections or preparations for implantation into muscle, hypodermis, organs and the like, preparations for administering to mucosa onto cavitas nasi, rectum, uterus and the like), oral preparations (e.g., capsules such as hard capsules and soft capsules, solid preparations such as granules and powders, solutions such as suspensions and the like) and the like.

In particular, the sustained-release preparation of the present invention is preferably for injection. For example, in case that the sustained-release preparation is a microcapsule, a practically useful sustained-release preparation for injection can be obtained by adding above-mentioned dispersing vehicle to the microcapsule to prepare an aqueous suspension. Further, a practically usable sustained-release preparation for injection can be obtained by adding above-mentioned oily dispersing vehicle to the microcapsule to prepare an oil suspension.

When the sustained-release preparation is, for example, a microcapsule, the particle size of the microcapsule for an injectable suspension may be within the range satisfying the requirements for the degree of dispersion and the needle passability for the injection. For example, the particle size is within the range of about 0.1 to about 300 μm, preferably about 1 to about 150 μm, more preferably about 2 to about 100 μm, as the average particle size.

Methods for preparing the above microcapsule as a sterile preparation include, but are not limited to, a method in which the entire production process is sterile, a method for sterilization in which the gamma rays are irradiated and a method in which an antiseptic is added.

The sustained-release preparation of the present invention is less toxic and can be safely used in mammals (e.g., human, cattle, pig, dog, cat, mouse, rat, rabbit and the like).

Indication of the sustained-release preparation varies variously depending on the bioactive substance used. The sustained-release preparation is useful to prevent or treat diabetes when the bioactive substance is insulin; viral hepatitis (e.g., hepatitis C, HBe antigen-positive active hepatitis and the like) and cancer (e.g., renal carcinoma, multiple myeloma and the like) when the bioactive substance is interferon-α; anemia (e.g., anemia during dialysis of kidney and the like) when the bioactive substance is erythropoietin; neutropenia (e.g., in cancer therapy) and infections when the bioactive substance is G-CSF; cancer (e.g., hemangioendothelioma and the like) when the bioactive substance is IL-2; fracture, wound (e.g., bedsore and the like), periodontitis and gastrointestinal ulcer when the bioactive substance is FGF; thrombocytopenia when the bioactive substance is FGF-9; senile dementia and neuropathy when the bioactive substance is NGF; thrombosis when the bioactive substance is TPA; and cancer when the bioactive substance is tumor necrosis factor. Further, the GH-containing sustained-release preparation can be applied to Turner's syndrome, chronic renal failure, achondroplasia (cartilage dystrophia), and adult hypopituitarisin (adult GHD), exhaustive diseases such as AIDS and the like, as well as GH secretion insufficient dwarfism, based on growth hormone action of GH. Further, it is reported that GH is applied to diseases such as Down syndrome, Silver syndrome, dysostosis and juvenile chronic arthritis to provide excellent therapeutic effects, therefore the GH-containing sustained-release preparation can be applied to these diseases. The GH-containing sustained-release preparation is also useful to prevent or treat congestive heart-failure and the like. The other indications to which the GH-containing sustained-release preparation can be applied include hematogenesis in organ transplantation or medication for an AIDS patient, improvement of hypoalimentation, renal anemia, angina pectoris, hyperlipidemia, obesity, acceleration of treatment for burn, wound or ulcer, early recovery from surgical invasion (operation, lesion)/postoperation, sepsis, prevention of fracture due to osteoporosis, early recovery of postoperative muscular power of a fracture patient due to osteoporosis, amyotropic lateral scelosis (ALS), decubitus and the like. Furthermore, it is expected to have effects as an antiaging agent aimed at improving the quality of life (QOL) for frail aged persons, or effects for suppressing the development of or improving neurodegenerative diseases (Alzheimer's disease, Parkinson's disease, cerebrovascular disease and the like) due to the nerve protective effect of hGH. By preparing GH into a sustained-release preparation, medicinal effects superior to those of a daily GH subcutaneous injection can be obtained for these indications.

Although varying depending on the kind and content of the bioactive substance, duration of the release, target disease, subject animal and the like, the dose of the sustained-release preparation may be any amount as long as the effective concentration of the bioactive substance in the body is maintained. For example, when the sustained-release preparation is the one designed for two week release, the dose of the bioactive substance can be suitably chosen from the range of preferably about 0.0001 to about 10 mg/kg body weight, more preferably about 0.05 to about 1 mg/kg body weight, per an adult. The administration frequency of the sustained-release preparation can be suitably chosen from once a week, once every two weeks, once a month, once every two months and the like, depending on the kind and content of the bioactive substance, the dosage form, duration of the release, target disease, subject animal and the like. One week-release to two months-release type sustained-release preparation is preferred and one week-release to one month-release type sustained-release preparation is more preferred.

When the bioactive substance as an active ingredient of the sustained-release preparation is, for example, insulin, the dose for an diabetic adult is suitably chosen from the range of usually about 0.001 to about 1 mg/kg body weight, preferably about 0.01 to about 0.2 mg/kg body weight, as an effective ingredient, and an administration of once a week is preferred.

When the bioactive substance as an active ingredient of the sustained-release preparation is GH, the dose may be any amount as long as the effective concentration of GH in the body is maintained, although varying depending on the kind and content of GH, duration of the release, target disease, subject animal and the like. In the treatment of the above described diseases, when the sustained-release preparation is a two week-release type preparation, the dose of GH can be suitably chosen from the range of about 0.01 to about 5 mg/kg body weight (about 0.03 to about 15 IU/kg body weight), more preferably about 0.05 to about 1 mg/kg body weight (about 0.15 to about 3 IU/kg body weight), per a infant or an adult for safe administration. The administration frequency can be suitably chosen from once a week, once every two weeks, once a month and the like, depending on the content of GH, the dosage form, duration of the release, target disease, subject animal and the like. One week-release to two months-release type sustained-release preparation is preferred, and one week-release to one month-release type sustained-release preparation is more preferred.

The sustained-release preparation is preferably stored at ordinary temperature or in a cold place. More preferably, the sustained-release preparation is stored in a cold place. The "ordinary temperature" and the "cold place" are defined in the Pharmacopoeia of Japan. Namely, the "ordinary temperature" means 15 to 25° C., and the "cold place" means a temperature of not more than 15° C. In the "cold place", a temperature of 2 to 8° C. is particularly preferred.

EXAMPLES

Hereinafter the present invention is explained more specifically with referring to the Reference Examples, Examples, Comparison Example and Test Examples, which do not limit the present invention.

Reference Example 1

To an aqueous solution of recombinanthGH (hGH concentration=2 mg/ml) was added ammonium acetate (20-fold mol equivalent). 100 ml of the resulting solution was added dropwise to the inner wall surface of an eggplant-type flask cooled in a dry ice-ethanol bath using a peristaltic pump for 30 min to freeze rapidly, and was dried in vacuo to give hGH powder. A lactic acid-glycolic acid copolymer (lactic acid/glycolic acid=65/35, viscosity=0.160 dL/g; 1.690 g) and zinc oxide (10 mg) were dissolved in dichloromethane (2.7 ml). To the organic solvent solution was added the above-mentioned hGH powder (300 mg) and the mixture was atomized with Polytron (manufactured by Kinematica). This S/O dispersion was added to a 0.1% aqueous solution of polyvinyl alcohol (800 ml) and the mixture was stirred and emulsified using a homomixer. The obtained emulsion was stirred at room temperature for 3 hr to evaporate dichloromethane and centrifuged (about 2,000 rpm) to collect microcapsules. The microcapsules were then washed twice with distilled water (400 ml), added D-mannitol (0.2 g) and freeze-dried. Furthermore, in order to remove the residual solvent, the microcapsules were dried in vacuo at 46° C. for 3 days to give hGH-containing microcapsules.

Reference Example 2

Mannitol (5 g), carboxymethylcellulose sodium (0.5 g) and Polysolvate 80 (0.1 g) were dissolved in distilled water for injection (about 90 mL). The pH of the solution was adjusted to pH 5 to 7 with acetic acid, and the solution was made up to 100 mL with distilled water for injection. The obtained solution was filtered with a filter having a pore size of 0.45 µm to give a dispersion vehicle for microcapsule injection.

Example 1

Mannitol (5 g), L-arginine hydrochloride (2 g), carboxymethylcellulose sodium (0.5 g) and Polysolvate 80 (0.1 g) were dissolved in distilled water for injection (about 90 mL). The pH of the solution was adjusted to pH 5 to 7 with acetic acid, and the solution was made up to 100 mL with distilled water for injection. The obtained solution was filtered with a filter having a pore size of 0.45 µm to give a dispersion vehicle for microcapsule injection.

Example 2

Mannitol (5 g), L-arginine hydrochloride (2 g) and Polysolvate 80 (0.1 g) were dissolved in distilled water for injection (about 60 mL). To the solution was added polyethyleneglycol 400 (30 mL), and the solution was made up to 100 mL with distilled water for injection. The obtained solution was filtered with a filter having a pore size of 0.45 µm to give a dispersion vehicle for microcapsule injection.

Example 3

Mannitol (5 g), benzalkonium chloride (0.1 g) and Polysolvate 80 (0.1 g) were dissolved in distilled water for injection (about 60 mL). To the solution was added polyethyleneglycol 400 (30 mL), and the solution was made up to 100 mL with distilled water for injection. The obtained solution was filtered with a filter having a pore size of 0.45 µm to give a dispersion vehicle for microcapsule injection.

Example 4

Mannitol (5 g), protamine sulfate (10 mg) and Polysolvate 80 (0.1 g) were dissolved in distilled water for injection (about 60 mL). To the solution was added polyethyleneglycol 400 (30 mL), and the solution was made up to 100 mL with distilled water for injection. The obtained solution was filtered with a filter having a pore size of 0.45 μm to give a dispersion vehicle for microcapsule injection.

Example 5

Mannitol (5 g), zinc chloride (42 mg) and Polysolvate 80 (0.1 g) were dissolved in distilled water for injection (about 60 mL). To the solution was added polyethyleneglycol 400 (30 mL), and the solution was made up to 100 mL with distilled water for injection. The obtained solution was filtered with a filter having a pore size of 0.45 μm to give a dispersion vehicle for microcapsule injection.

Example 6

Mannitol (5 g), lysine hydrochloride (1.7 g) and Polysolvate 80 (0.1 g) were dissolved in distilled water for injection (about 60 mL). To the solution was added polyethyleneglycol 400 (30 mL), and the solution was made up to 100 mL with distilled water for injection. The obtained solution was filtered with a filter having a pore size of 0.45 μm to give a dispersion vehicle for microcapsule injection.

Example 7

Mannitol (5 g), water-soluble chitosan (manufactured by PRONOVA, ultra pure grade, hydrochloride, CL113; 10 mg) and Polysolvate 80 (0.1 g) were dissolved in distilled water for injection (about 60 mL). To the solution was added polyethyleneglycol 400 (30 mL), and the solution was made up to 100 mL with distilled water for injection. The obtained solution was filtered with a filter having a pore size of 0.45 μm to give a dispersion vehicle for microcapsule injection.

Example 8

Mannitol (5 g) and Polysolvate 80 (0.1 g) were dissolved in distilled water for injection (about 60 mL) To the solution was added polyethyleneglycol 400 (30 mL), and the solution was made up to 100 mL with distilled water for injection. The obtained solution was filtered with a filter having a pore size of 0.45 μm to give a dispersion vehicle for microcapsule injection.

Example 9

To an aqueous solution of recombinanthGH (hGH concentration=2 mg/ml) was added ammonium acetate (20-fold mol equivalent). 100 ml of the resulting solution was added dropwise to the inner wall surface of an eggplant-type flask cooled in a dry ice-ethanol bath using a peristaltic pump for 30 min to freeze rapidly, and was dried in vacuo to give hGH powder. A lactic acid-glycolic acid copolymer (lactic acid/glycolic acid=65/35, viscosity=0.160 dL/g; 1.690 g) and zinc oxide (10 mg) were dissolved in dichloromethane (2.7 ml). To the organic solvent solution was added the above-mentioned hGH powder (300 mg) and the mixture was atomized with Polytron (manufactured by Kinematica). This S/O dispersion was added to a 0.1% aqueous solution of polyvinyl alcohol (800 ml) and the mixture was stirred and emulsified using a homomixer. The obtained emulsion was stirred at room temperature for 3 hr to evaporate dichloromethane and centrifuged (about 2,000 rpm) to collect microcapsules. The microcapsules were then washed twice with distilled water (400 ml), added D-mannitol (0.2 g) and protamine sulfate (0.4 mg) and freeze-dried. Furthermore, in order to remove the residual solvent, the microcapsules were dried in vacuo at 46° C. for 3 days to give hGH-containing microcapsules.

Example 10

To an aqueous solution of recombinant hGH (hGH concentration=2 mg/ml) was added ammonium acetate (20-fold mol equivalent). 100 ml of the resulting solution was added dropwise to the inner wall surface of an eggplant-type flask cooled in a dry ice-ethanol bath using a peristaltic pump for 30 min to freeze rapidly, and was dried in vacuo to give hGH powder. A lactic acid-glycolic acid copolymer (lactic acid/glycolic acid=65/35, viscosity=0.160 dL/g; 1.690 g) and zinc oxide (10 mg) were dissolved in dichloromethane (2.7 ml). To the organic solvent solution was added the above-mentioned hGH powder (300 mg) and the mixture was atomized with Polytron (manufactured by Kinematica). This S/O dispersion was added to a 0.1% aqueous solution of polyvinyl alcohol (800 ml) and the mixture was stirred and emulsified using a homomixer. The obtained emulsion was stirred at room temperature for 3 hrs to evaporate dichloromethane and centrifuged (about 1,500 rpm) to collect microcapsules. The microcapsules were then washed twice with distilled water (400 ml), added D-mannitol (0.2 g) and L-arginine hydrochloride (0.25 g) and freeze-dried. Furthermore, in order to remove the residual solvent, the microcapsules were dried in vacuo at 46° C. for 3 days to give hGH-containing microcapsules.

Example 11

To an aqueous solution of recombinant hGH (hGH concentration=2 mg/ml) was added ammonium acetate (20-fold mol equivalent). 100 ml of the resulting solution was added dropwise to the inner wall surface of an eggplant-type flask cooled in a dry ice-ethanol bath using a peristaltic pump for 30 min to freeze rapidly, and was dried in vacuo to give hGH powder. A lactic acid-glycolic acid copolymer (lactic acid/glycolic acid=65/35, viscosity=0.160 dL/g; 1.690 g) and zinc oxide (10 mg) were dissolved in dichloromethane (2.7 ml). To the organic solvent solution was added the above-mentioned hGH powder (300 mg) and the mixture was atomized with Polytron (manufactured by Kinematica). This S/O dispersion was added to a 0.1% aqueous solution of polyvinyl alcohol (800 ml) and the mixture was stirred and emulsified using a homomixer. The obtained emulsion was stirred at room temperature for 3 hrs to evaporate dichloromethane and centrifuged (about 1,500 rpm) to collect microcapsules. The microcapsules were then washed twice with distilled water (400 ml), added D-mannitol (0.2 g) and N-methylglucamine (0.25 g) and freeze-dried. Furthermore, in order to remove the residual solvent, the microcapsules were dried in vacuo at 46° C. for 3 days to give hGH-containing microcapsules.

Example 12

The microcapsules containing protamine sulfate obtained in Example 9 were filled in a Teflon tube having an inner diameter of 2.0 mm and heated at 60° C. for 15 min. After heating, the microcapsules were compressed with a rod, cooled and formed to give a rod-shaped preparation having an outer diameter of 2.0 mm and a length of about 1 cm.

Example 13

Mannitol (5 g), L-arginine hydrochloride (0.2 g), carboxymethylcellulose sodium (0.5 g) and Polysolvate 80 (0.1 g) were dissolved in distilled water for injection (about 90 mL). The pH of the solution was adjusted to pH 5 to 7 with acetic acid, and the solution was made up to 100 mL with distilled water for injection. The obtained solution was filtered with a filter having a pore size of 0.45 μm to give a dispersion vehicle for microcapsule injection.

Example 14

Mannitol (5 g), L-arginine hydrochloride (1.2 g), carboxymethylcellulose sodium (0.5 g) and Polysolvate 80 (0.1 g) were dissolved in distilled water for injection (about 90 mL). The pH of the solution was adjusted to pH 5 to 7 with acetic acid, and the solution was made up to 100 mL with distilled water for injection. The obtained solution was filtered with a filter having a pore size of 0.45 μm to give a dispersion vehicle for microcapsule injection.

Example 15

Mannitol (5 g), L-arginine hydrochloride (2.4 g), carboxymethylcellulose sodium (0.5 g) and Polysolvate 80 (0.1 g) were dissolved in distilled water for injection (about 90 mL). The pH of the solution was adjusted to pH 5 to 7 with acetic acid, and the solution was made up to 100 mL with distilled water for injection. The obtained solution was filtered with a filter having a pore size of 0.45 μm to give a dispersion vehicle for microcapsule injection.

Example 16

Mannitol (1.5 g), L-arginine hydrochloride (2.4 g), carboxymethylcellulose sodium (0.5 g) and Polysolvate 80 (0.1 g) were dissolved in distilled water for injection (about 90 mL), and the solution was made up to 100 mL with distilled water for injection. The obtained solution was filtered with a filter having a pore size of 0.45 μm to give a dispersion vehicle for microcapsule injection.

Example 17

Mannitol (5 g), lysine hydrochloride (2.1 g), carboxymethylcellulose sodium (0.5 g) and Polysolvate 80 (0.1 g) were dissolved in distilled water for injection (about 90 mL), and the solution was made up to 100 mL with distilled water for injection. The obtained solution was filtered with a filter having a pore size of 0.45 μm to give a dispersion vehicle for microcapsule injection.

Example 18

Mannitol (5 g), N-methylglucamine (1 g), methylcellulose (0.5 g) and Polysolvate 80 (0.1 g) were dissolved in distilled water for injection (about 90 mL). The pH of the solution was adjusted to 6 with hydrochloric acid, and the solution was made up to 100 mL with distilled water for injection. The obtained solution was filtered with a filter having a pore size of 0.45 μm to give a dispersion vehicle for microcapsule injection.

Example 19

Mannitol (5 g), zinc acetate (1 g), methylcellulose (0.5 g) and Polysolvate 80 (0.1 g) were dissolved in distilled water for injection (about 90 mL), and the solution was made up to 100 mL with distilled water for injection. The obtained solution was filtered with a filter having a pore size of 0.45 μm to give a dispersion vehicle for microcapsule injection.

Example 20

Mannitol (5 g), water-soluble chitosan (manufactured by PRONOVA, ultra pure grade, hydrochloride, CL113; 0.1 g), methylcellulose (0.5 g) and Polysolvate 80 (0.1 g) were dissolved in distilled water for injection (about 90 mL), and the solution was made up to 100 mL with distilled water for injection. The obtained solution was filtered with a filter having a pore size of 0.45 μm to give a dispersion vehicle for microcapsule injection.

Example 21

To an aqueous solution of recombinant hGH containing sodium (9.6 μg/mL) (hGH concentration=2 mg/ml) was added ammonium acetate (20-fold mol equivalent). 100 ml of the resulting solution was added dropwise to the inner wall surface of an eggplant-type flask cooled in a dry ice-ethanol bath using a peristaltic pump for 30 min to freeze rapidly, and was dried in vacuo to give hGH powder. A lactic acid-glycolic acid copolymer (lactic acid/glycolic acid=65/35, viscosity=0.160 dL/g; 1.690 g) and zinc oxide (10 mg) were dissolved in dichloromethane (2.7 ml). To the organic solvent solution was added the above-mentioned hGH powder (300 mg) and the mixture was atomized with Polytron (manufactured by Kinematica). This S/O dispersion was added to a 0.1% aqueous solution of polyvinyl alcohol (800 ml) and the mixture was stirred and emulsified using a homomixer. The obtained emulsion was stirred at room temperature for 3 hrs to evaporate dichloromethane and centrifuged (about 2,000 rpm) to collect microcapsules. The microcapsules were then washed twice with distilled water (400 ml), added D-mannitol (0.2 g) and freeze-dried. Furthermore, in order to remove the residual solvent, the microcapsules were dried in vacuo at 46° C. for 3 days to give hGH-containing microcapsules.

Example 22

Using an aqueous solution of recombinant hGH (hGH concentration=2 mg/mL) containing sodium (7.3 μg/mL), hGH-containing microcapsules were obtained according to the similar method to Example 21.

Comparison Example 1

Using an aqueous solution of recombinant hGH (hGH concentration=2 mg/mL) containing sodium (16.3 μg/mL), hGH-containing microcapsules were obtained according to the similar method to Example 21.

Test Example 1

Using a suspension obtained by adding the dispersion vehicle produced in Example 1 to the hGH-containing microcapsules obtained in Reference Example 1, the following tests were carried out.
(1) In Vivo Release in Rat
A SD rat (male, 6 week-old) was subjected to immunosuppression treatment with tacrolimus. Prograf injection (manufactured by Fujisawa Pharmaceutical Co., Ltd., 5 mg) was diluted with saline. The dilution was administered subcutaneously at the dose of 0.4 mg/0.2 ml/rat (three days before the administration of the microcapsule), 0.2 mg/0.2 ml/rat (immediately after the administration of microcapsule, and on the 4th, 7th and 11th days after the administration of the microcapsule) and 0.3 mg/0.2 ml/rat (on the 14th, 18th, 21st, 25th, 28th and 32nd days after the administration of the microcapsule), respectively, which suppressed the production of antibody to hGH and allowed the evaluation of the hGH concentration in rat blood serum for 5 weeks after the administration of the microcapsule.

The microcapsules obtained in Reference Example 1 were suspended in a dispersion vehicle produced in Example 1 at the concentration of 16 mg hGH/ml. The obtained suspension (0.75 ml) was administered subcutaneously to the back of the rat under ether anesthesia. The dose was 12 mg as hGH. After the administration of the microcapsule, blood was sequentially collected from the tail vein and serum was collected. The concentration of hGH in serum was measured by immunoradiometric assay (Ab beads HGH, Eiken Chemical Co., Ltd.).

(2) Initial Release Rate

To the immunosuppressed SD rat was administered subcutaneously a solution of hGH at the dose of 5, 10 and 20 mg/kg, respectively, and blood was sequentially collected and the concentration of hGH in serum was measured. AUC was calculated by trapezoid method. From the AUC up to 24 hrs after administration of the microcapsule, the dose of hGH, which corresponds to that for the subcutaneous administration of the hGH solution, was calculated, and then the dose obtained was divided by the dose of microcapsules (12 mg) to calculate the initial release percentage.

The initial release percentage for the group in which the suspension containing the dispersion vehicle of Example 1 had been administered, was 6%. As is apparent from this result, the initial release for the group administered the microcapsule in which the L-arginine hydrochloride-containing dispersion vehicle was used, was small, and high blood concentration of hGH was maintained over one month.

Test Example 2

Using suspensions obtained by adding the dispersion vehicle prepared in Example 2, Example 3, Example 4 or Example 5, respectively, to the hGH-containing microcapsule obtained in Reference Example 1, the following tests were carried out.

(1) In Vivo Release in Rat

The serum level profile of hGH in immunosuppressed SD rats was evaluated according to the similar operation to Test Example 1 (1).

(2) Initial Release Rate

The initial release percentage for an immunosuppressed SD rat was evaluated according to the similar operation to Test Example 1 (2).

The initial release percentage in each of the groups administered the suspension in which the dispersion vehicle of Example 2, Example 3, Example 4 or Example 5 had been added, was 5%, 6%, 3% and 7%, respectively. As is apparent from this result, the initial release for the groups administered the microcapsule in which a dispersion vehicle containing L-arginine hydrochloride, benzalkonium chloride, protamine sulfate or zinc chloride was used, was small, and high blood concentration of hGH was maintained over one month. Therefore, it was revealed that the dispersion vehicle containing a basic substance or a water-soluble multivalent metal salt had an effect of suppressing the initial release.

Test Example 3

Using a suspension obtained by adding the dispersion vehicle prepared in Reference Example 2 to the hGH-containing microcapsules obtained in Example 9, the following tests were carried out.

(1) In Vivo Release in Rat

The serum level profile of hGH in immunosuppressed SD rats was evaluated according to the similar operation to Test Example 1 (1).

(2) Initial Release Rate

The initial release percentage for an immunosuppressed SD rat was evaluated according to the similar operation to Test Example 1 (2).

The initial release percentage in the group administered the suspension in which the dispersion vehicle of Reference Example 2 had been added to the hGH-containing microcapsules obtained in Example 9, was 8%. As is apparent from this result, the initial release for the group administered the sustained release microcapsule which retains protamine sulfate, that is a basic substance, on the surface of the matrix, was small, and high blood concentration of hGH was maintained over one month.

Test Example 4

Using suspensions obtained by adding the dispersion vehicle prepared in Example 8 to the hGH-containing microcapsules obtained in Reference Example 1 and Example 10, respectively, the following tests were carried out.

(1) In Vivo Release in Rat

The serum level profile of hGH in immunosuppressed SD rats was evaluated according to the similar operation to Test Example 1 (1).

(2) Initial Release Rate

The initial release percentage for an immunosuppressed SD rat was evaluated according to the similar operation to Test Example 1 (2).

The initial release percentage in each of the groups administered the suspension in which the dispersion vehicle of Example 8 had been added to the hGH-containing microcapsule obtained in Reference Example 1 and Example 10, respectively, was 7% and 5%, respectively. As is apparent from this result, the initial release for the group administered the sustained-release microcapsule preparation which was suspended with a dispersion vehicle containing polyethylene glycol 400, that is a polyol, was small, and high blood concentration of hGH was maintained over one month.

Test Example 5

Using suspensions obtained by adding the dispersion vehicle prepared in Example 13, Example 14 or Example 15, to the hGH-containing microcapsules obtained in Reference Example 1; respectively, the following tests were carried out.

(1) In Vivo Release in Rat

The serum level profile of hGH in immunosuppressed SD rats was evaluated according to the similar operation to Test Example 1 (1).

(2) Initial Release Rate

The initial release percentage for an immunosuppressed SD rat was evaluated according to the similar operation to Test Example 1 (2).

The initial release percentage in each of the groups administered the suspensions which were obtained by adding the dispersion vehicle of Example 13, Example 14 or Example 15, respectively, was 11%, 7% and 6%, respectively. As is apparent from this result, the initial release for the group administered the microcapsule in which the dispersion vehicle containing L-arginine hydrochloride was used, decreased in accordance with the increase of the amount of the addition, and high blood concentration of hGH was maintained over one month. Therefore, the effect of suppressing the initial release depending on the amount of L-arginine hydrochloride in the dispersion vehicle has become clear.

Test Example 6

Using a suspension obtained by adding the dispersion vehicle prepared in Example 16 to the hGH-containing microcapsules obtained in Reference Example 1, the following tests were carried out.

(1) In Vivo Release in Rat

The serum level profile of hGH in immunosuppressed SD rats was evaluated according to the similar operation to Test Example 1 (1).

(2) Initial Release Rate

The initial release percentage for an immunosuppressed SD rat was evaluated according to the similar operation to Test Example 1 (2).

The initial release percentage in the group administered the suspension which was obtained by adding the dispersion vehicle of Example 16, was 4%. As is apparent from this result, the initial release of the group administered the microcapsule in which a dispersion vehicle containing L-arginine hydrochloride was used, was small even though the amount of mannitol was decreased in order to make the dispersion vehicle isotonic, and high blood concentration of hGH was maintained over one month. It was revealed that the effect for suppressing the initial release depended on the amount of L-arginine hydrochloride, and that the decrease of the amount of mannitol did not affect the effect.

Test Example 7

Using the suspensions obtained by adding the dispersion vehicle prepared in Example 17, Example 18, Example 19 or Example 20, respectively, to the hGH-containing microcapsules obtained in Reference Example 1, the following tests were carried out.

(1) In Vivo Release in Rat

The serum level profile of hGH in immunosuppressed SD rats was evaluated according to the similar operation to Test Example 1 (1).

(2) Initial Release Rate

The initial release percentage for an immunosuppressed SD rat was evaluated according to the similar operation to Test Example 1 (2).

The initial release percentage in each of the groups administered the suspension which was obtained by adding the dispersion vehicle of Example 17, Example 18, Example 19 or Example 20, was 8%, 11%, 10% and 7%, respectively. As is apparent from this result, the initial release for the groups administered the microcapsule in which the dispersion vehicle containing lysine hydrochloride, N-methylglucamine, zinc acetate or chitosan was used, was small, and high blood concentration of hGH was maintained over one month. Therefore, it was revealed that the dispersion vehicle containing the basic substance, water-soluble multivalent metal salt or basic polysaccharide had an effect for suppressing the initial release.

Test Example 8

For the hGH-containing microcapsules obtained Example 21 or Comparison Example 1, the following tests were carried out.

(1) Weight-Average Particle Diameter of hGH in Dichloromethane

The hGH was dispersed in dichloromethane using a homogenizer (Polytron (manufactured by Kinematica)) at about 20,000 rpm, for about 30 seconds and diluted to the suitable range in which the mean particle diameter can be measured using a laser diffraction particle size analyzer (SALD2000A: manufactured by Shimadzu Corporation), and the weight-average particle diameter was measured.

(2) hGH Entrapment Efficiency in Microcapsules

To the microcapsules (10 mg) was added acetonitrile (1.75 mL), and the mixture was subjected to sonication. To the obtained acetonitrile solution was added 10 mM phosphate buffered saline (pH 8.0, 3.25 mL), and the mixture was again subjected to sonication to extract hGH, that is an active component. The hGH extraction solution was then subjected to size-exclusion high performance liquid chromatography under the following condition to measure the content of hGH, and the encapsulation ratio was calculated therefrom.

Column: TSK gel G 3000SW$_{XL}$ (manufactured by Tosoh)
Eluant: 50 mM $NH_4HCO_3$
Flow rate: 0.6 mL/min
Detection wavelength: 214 nm (3) Initial Release Rate The initial release percentage for an immunosuppressed SD rat was evaluated according to the similar procedure to Test Example 1(2).

For Example 21 and Comparison Example 1, the weight-average particle diameter of hGH in dichloromethane was 1.2 μm and 2.4 μm respectively, the hGH entrapment efficiency in microcapsules was 85% and 73% respectively, and the initial release percentage in an immunosuppression rat was 18% and 40% respectively. As is apparent from these results, by adjusting the sodium concentration in a human growth hormone solution to not more than about 10 μg/mL, microparticles of the human growth hormone having the weight-average particle diameter of about 0.5 μm to about 2.0 μm could be obtained, and microcapsules having high hGH entrapment efficiency and small initial release were obtained. Namely, it was revealed that, by lowering the salt concentration in a bioactive substance solution, a sustained-release preparation in which a drug was micronized, and which has a high entrapment efficiency and a suppressed initial release, can be obtained.

Test Example 9

For the hGH-containing microcapsule obtained in Example 22, the following tests were carried out.

(1) Weight-Average Particle Diameter of hGH in Dichloromethane

The weight-average particle diameter of hGH in dichloromethane was evaluated according to the similar operation to Test Example 8(1).

(2) hGH Entrapment Efficiency in Microcapsules

The hGH entrapment efficiency in microcapsules was evaluated according to the similar operation to Test Example 8(2).

(3) Initial Release Rate

The initial release percentage for an immunosuppressed SD rat was evaluated according to the similar operation to Example 1 (2).

For Example 22, the weight-average particle diameter of hGH in dichloromethane was 1.2 µm, the hGH entrapment efficiency in microcapsules was 83%, and the initial release percentage in an immunosuppressed rat was 14%. As is apparent from these results, by adjusting the sodium concentration in a human growth hormone solution to not more than about 10 µg/mL, fine particles of the human growth hormone having the weight-average particle diameter of about 0.5 µm to about 2.0 µm could be obtained and microcapsules having high hGH entrapment efficiency and small initial release were obtained. Namely, it was revealed that, by lowering the salt concentration in a bioactive substance solution, a sustained-release preparation in which a drug was micronaized, and which has a high entrapment efficiency and a suppressed initial release, can be obtained.

INDUSTRIAL APPLICABILITY

According to the present invention, by adding a basic substance or a water-soluble multivalent metal salt to the outer portion of a matrix or a dispersion vehicle thereof, a sustained-release preparation having very superior clinical characteristics as a medicament, in which the initial release of a bioactive substance immediately after administration is remarkably suppressed, a constant amount of the bioactive substance is released after administration over a prolonged period of time, and deterioration of the bioactive substance and the residual organic solvent are extremely decreased, can be obtained.

The invention claimed is:

1. A sustained-release preparation wherein the initial release of a bioactive substance is suppressed, comprising a combination of a microcapsule containing the bioactive substance and a biodegradable polymer having a weight-average molecular weight of about 3,000 to about 50,000, and a dispersion vehicle containing a basic amino acid and a polyethyleneglycol, wherein the dispersion vehicle is a water-soluble medium for suspension of the microcapsule used for injection and the basic amino acid and the polyethyleneglycol do not exist in the microcapsule and exist outside the microcapsule or on the outer surface of the microcapsule;

and wherein the basic amino acid and polyethyleneglycol suppress the initial release of the bioactive substance.

2. The sustained-release preparation according to claim 1, wherein the basic amino acid is arginine or lysine.

3. The sustained-release preparation according to claim 1, wherein the bioactive substance is a bioactive peptide.

4. The sustained-release preparation according to claim 3, wherein the bioactive peptide has a molecular weight of about 200 to about 500,000.

5. The sustained-release preparation according to claim 3, wherein the bioactive peptide has a molecular weight of about 5,000 to about 500,000.

6. The sustained-release preparation according to claim 3, wherein the bioactive peptide is a hormone, a cytokine, a hematopoietic factor, a growth factor or an enzyme.

7. The sustained-release preparation according to claim 3, wherein the bioactive peptide is a human growth hormone.

8. The sustained-release preparation according to claim 1, wherein the biodegradable polymer is a homopolymer or a copolymer of α-hydroxycarboxylic acids, or a mixture thereof.

9. The sustained-release preparation according to claim 1, wherein the biodegradable polymer is a copolymer having a composition ratio of lactic acid/glycolic acid of about 100/0 to about 40/60 mol %.

10. The sustained-release preparation according to claim 1, wherein the biodegradable polymer is a homopolymer of lactic acid.

11. A dispersion vehicle containing a basic amino acid and a polyethyleneglycol, which is for the production of the sustained-release preparation used for injection according to claim 1.

12. The sustained-release preparation according to claim 1, wherein the bioactive substance is a powder obtained by lyophilization of a solution containing the bioactive substance whose concentration of an alkaline metal ion is adjusted to not more than about 10 µg/mL.

13. The sustained-release preparation according to claim 12, wherein the powder is a microparticle.

14. The sustained-release preparation according to claim 13, wherein the weight-average particle diameter of the powder is about 0.5 µm to about 2.0 µm.

15. The sustained-release preparation according to claim 12, wherein the bioactive substance is a bioactive peptide.

16. The sustained-release preparation according to claim 12, wherein the bioactive peptide is a hormone, a cytokine, a hematopoietic factor, a growth factor or an enzyme.

17. The sustained-release preparation according to claim 12, wherein the bioactive peptide is a human growth hormone.

18. A method for suppressing the initial release of a bioactive substance in a sustained release preparation, comprising mixing a dispersion vehicle containing a basic amino acid and a polyethyleneglycol with a microcapsule containing the bioactive substance and a biodegradable polymer having a weight-average molecular weight of about 3,000 to about 50,000, wherein the dispersion vehicle is a water-soluble medium for suspension of the microcapsule containing the bioactive substance and the biodegradable polymer used for injection; and said sustained-release preparation comprises a combination of the microcapsule and the dispersion vehicle, and the basic amino acid and the polyethyleneglycol in the sustained-release preparation do not exist in the microcapsule and exist outside the microcapsule or on the outer surface of the microcapsule;

and wherein the basic amino acid and polyethyleneglycol suppress the initial release of the bioactive substance.

* * * * *